United States Patent [19]

Spector et al.

[11] Patent Number: 4,535,482
[45] Date of Patent: Aug. 20, 1985

[54] HEATED GLOVE

[76] Inventors: George Spector, c/o George Spector, 3615 Woolworth Bldg., 233 Broadway; Lesley Spector, 3615 Woolworth Bldg., 233 Broadway, both of New York, N.Y. 10007

[21] Appl. No.: 460,750
[22] Filed: Jan. 24, 1983
[51] Int. Cl.³ .............................................. A41D 19/00
[52] U.S. Cl. ....................................... 2/160; 2/161 A; 2/163
[58] Field of Search ............... 2/158, 160, 161 A, 163; 36/44, 2.6; 44/3 A

[56] References Cited

U.S. PATENT DOCUMENTS

| 2,103,594 | 12/1937 | Murray | 2/160 |
| 2,685,021 | 7/1954 | Duncan | 2/158 X |
| 3,632,966 | 1/1972 | Arron | 2/158 X |
| 4,249,319 | 2/1981 | Yoshida | 36/2.6 |
| 4,281,418 | 8/1981 | Cieslak et al. | 2/160 |
| 4,331,731 | 5/1982 | Seike et al. | 36/2.6 |
| 4,373,274 | 2/1983 | Michalski | 36/2.6 |

Primary Examiner—Louis K. Rimrodt

[57] ABSTRACT

A heated glove utilizing a hand warmer is provided and consists of an inner layer of insulated material, a middle layer of waterproof material and an outer layer of leather material. The inner layer has a sealable top pocket to hold the hand warmer and five ducts for allowing heat to travel from the hand warmer to top of each finger tip of the hand.

5 Claims, 7 Drawing Figures

HEATED GLOVE

BACKGROUND OF THE INVENTION

The instant invention relates generally to gloves and more specifically it relates to a heated glove utilizing a hand warmer of conventional fuel burning type such as the JON-WARMER made by ALADDIN MFG Co., INC.

In the winter when a person is outdoors, skiing, hunting or doing any other activity the gloves that they wear will not always keep their hands warm. The finger tips are the first that freezes in very cold weather, creating a dangerous situation. This is not desirable so accordingly it is in need of an improvement.

SUMMARY OF THE INVENTION

A principle object of the present invention is to provide a heated glove utilizing a hand warmer that allows heat to travel from the hand warmer to top of each finger tip of the hand in the heated glove.

Another object is to provide a heated glove utilizing a hand warmer that fits into a top pocket and five ducts, each extending over each finger from the top pocket within the heated glove.

An additional object is to provide a heated glove utilizing a hand warmer in a sheath, the sheath insertable into a normal glove to make it a heated glove.

A further object is to provide a heated glove utilizing a hand warmer that is simple and easy to use.

A still further object is to provide heated glove utilizing a hand warmer that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
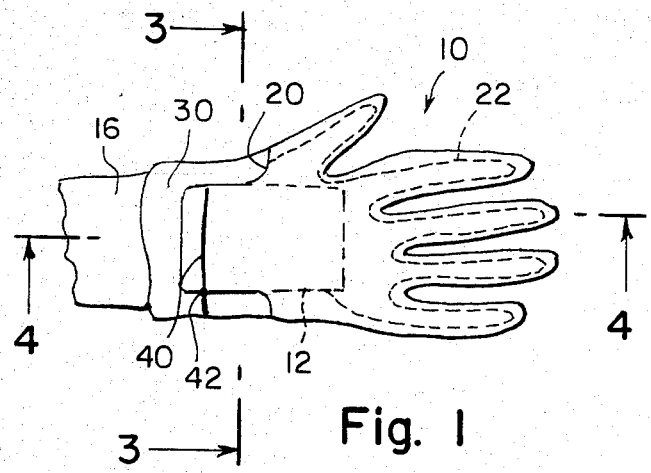
FIG. 1 is a top view of the invention in use.
Figure 2:
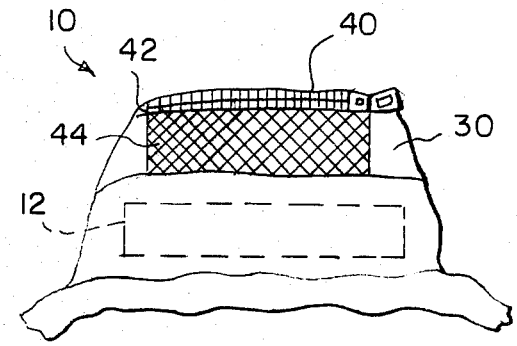
FIG. 2 is a partial front elevational view.
Figure 3:
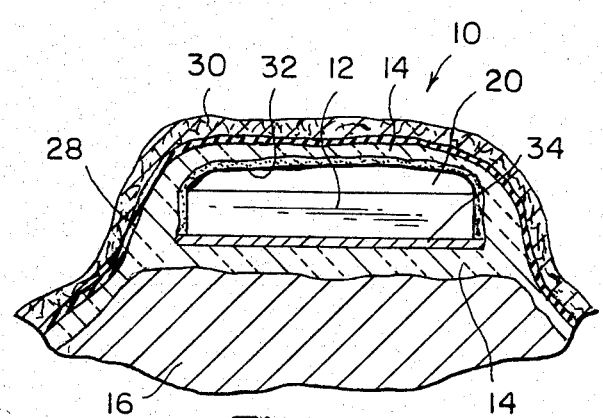
FIG. 3 is a partial cross sectional view taken along line 3—3 in FIG. 1.

Turning now descriptively to the drawings, in which similar reference characters denote similar elements throughout the several views, FIGS. 1 through 4 illustrate a heated glove 10 utilizing a hand warmer 12. The heated glove 10 contains an inner layer 14 of insulated material placed around a hand 16 and fingers 18. The inner layer 14 forms a sealable top pocket 20 to hold the hand warmer 12 and five ducts 22. Each duct 22 extends from the top pocket 20 over each finger 18 and having a plurality of holes 24 above each finger tip 26.

A middle layer 28 of waterproof material is placed around the inner layer 14 while an outer layer 30 of leather material is placed around the middle layer 28 to form the heated glove 10.

A top layer 32 of heat reflecting material is placed within the top pocket 20 above the hand warmer 12 and each of the five ducts 22. The top layer 32 will reflect the heat back into the top pocket 20 and the ducts 22.

A bottom layer 34 of heat conducting material is placed within the top pocket 20 below the hand warmer 12 and each of the five ducts 22. The bottom layer 34 has a plurality of holes 36 in line with the holes 24 of the inner layer 14 of insulated material. The bottom layer 34 can take the heat within the top pocket 20 through each of the five ducts 22.

A stiff support member 38 is placed between the top layer 32 and bottom layer 34 of each duct 22 to keep the ducts 22 open. The heat can travel along the ducts 22 to heat the top of the finger tips 26 of the hand 16 via the holes 36 and 24.

A zipper 40 is placed along a closure line 42 in the outer layer 30 so that the top pocket 20 in the inner layer 14 can accommodate the hand warmer 12. A mesh screen 44 is placed below the zipper 40 on the closure line 42 in the outer layer 30 to allow ambient air as indicated by arrow 46, to enter the top pocket 20 to supply oxygen to the hand warmer 12.

Figure 5:
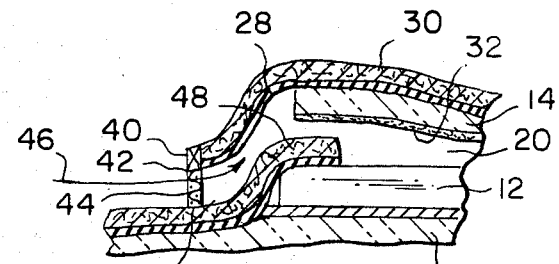
FIG. 5 is a partial side cross sectional view of a modification.
Figure 4:
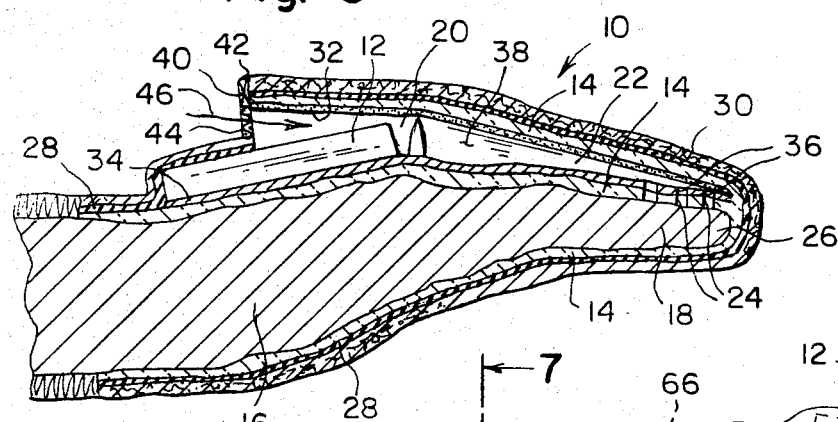
FIG. 4 is a cross sectional view taken along line 4—4 in FIG. 1.

FIG. 5 shows a modification whereby the zipper 40 is in the rear of the hand warmer 12 along a closure line 42 in the outer layer 30. The outer layer 30 overlaps the hand warmer 12 at 48. A mesh screen 44 is placed below the zipper 40 on the closure line 42 and connected to the overlap 48 at 50 to allow ambient air as indicated by arrow 46 to enter the top pocket 20 to supply oxygen to the hand warmer 12.

Figure 7:
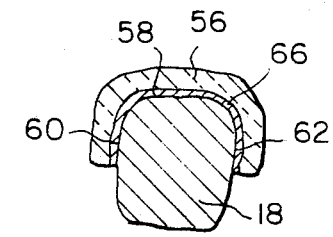
FIG. 7 is a cross sectional view taken along line 7—7 in FIG. 6.
Figure 6:
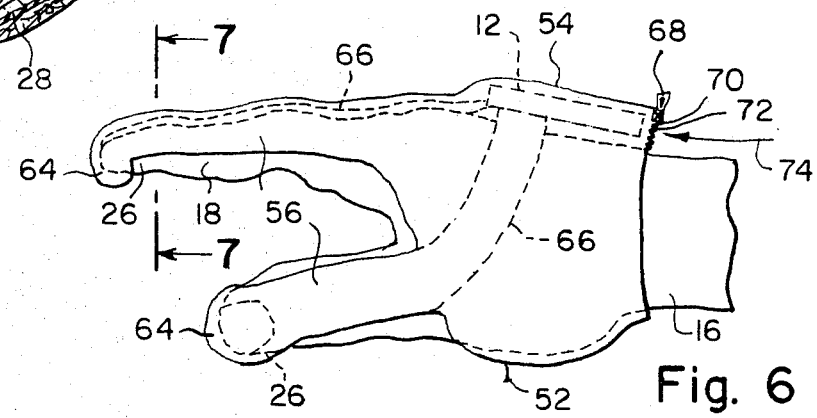
FIG. 6 is a side view of another modification showing a sheath.

FIGS. 6 and 7 shows another modification. A sheath 52 of insulated material is placed around a hand 16. The sheath 52 has a sealable top pocket 54 to hold the hand warmer 12 and five finger projections 56. Each projection 56 covers a top 58 and two sides 60 and 62 of a finger 18 with an end 64 of the projection 56 engaging a finger tip 26.

A strip 66 of conductive material is placed between each of the finger projections 56 and the fingers 18 and extends from the hand warmer 12 in the top pocket 54. Each strip 60 of conductive material can carry heat from the hand warmer 12 over the top 58 and two sides 60 and 62 of the finger 18. The sheath 52 is insertable into a normal glove (not shown) to make it a heated glove.

A zipper 68 is placed along a rear closure line 70 of the top pocket 54 so that the top pocket 54 can accommodate the hand warmer 12. A mesh screen 72 is placed below the zipper 68 to allow ambient air as indicated by arrow 74 to enter the top pocket 54 to supply oxygen to the hand warmer 12.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A heated glove for utilizing a hand warmer which comprises:
   (a) an inner layer of insulated material placed around a hand and fingers, the inner layer forming a sealable top pocket to hold the hand warmer and five ducts, each duct extending from the top pocket over each finger and having a plurality of holes above each finger tip;
   (b) a middle layer of waterproof material placed around the inner layer;
   (c) an outer layer of leather material placed around the middle layer to form the heated glove; and
   (d) means for allowing heat to travel from the hand warmer to top of each finger tip of the hand in the heated glove.

2. A heated glove as recited in claim 1, wherein the means for allowing heat to travel from the hand warmer to top of each finger tip of the hand in the heated glove comprises:
   (a) a top layer of heat reflecting material placed within the top pocket above the hand warmer and each of the five ducts so that the top layer will reflect the heat back into the top pocket and the ducts;
   (b) a bottom layer of heat conducting material placed within the top pocket below the hand warmer and each of the five ducts, the bottom layer having a plurality of holes in line with the holes of the inner layer of insulated material so that the bottom layer can take the heat within the top pocket through each of the five ducts; and
   (c) five stiff support members, each stiff support member placed between the top layer and bottom layer of the ducts to keep the duct open so that the heat can travel along the duct to heat the top of the finger tips of the hand via the holes.

3. A heated glove as recited in claim 2, that further comprises:
   (a) a zipper placed along a closure line in the outer layer so that the top pocket in the inner layer can accommodate the hand warmer; and
   (b) a mesh screen placed below the zipper on the closure line in the outer layer to allow ambient air to enter the top pocket to supply oxygen to the hand warmer.

4. A heated glove for utilizing a hand warmer which comprises:
   (a) a sheath of insulated material placed around a hand, the sheath having a sealable top pocket to hold the hand warmer and five finger projecting each projection covers a top and two sides of a finger with an end of the projection engaging a finger tip;
   (b) five strips of conductive material each strip of conductive material placed between the finger projection and the finger and extending from the hand warmer in the top pocket so that the stip of conductive material can carry heat from the hand warmer over the top and two sides of the finger, the sheath insertable into a normal glove to make it a heated glove.

5. A heated glove as recited in claim 4, wherein the sealable top pocket in the sheath further comprises:
   (a) a zipper placed along a rear closure line of the top pocket so that the top pocket can accommodate the hand warmer; and
   (b) a mesh screen placed below the zipper to allow ambient air to enter the top pocket to supply oxygen to the hand warmer.

* * * * *